US009265865B2

(12) United States Patent
Hixon et al.

(10) Patent No.: US 9,265,865 B2
(45) Date of Patent: Feb. 23, 2016

(54) STENT HAVING TIME-RELEASE INDICATOR

(75) Inventors: Jessica Hixon, Watertown, MA (US); Bryan Kostelac, Camby, IN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1752 days.

(21) Appl. No.: 11/428,014

(22) Filed: Jun. 30, 2006

(65) Prior Publication Data

US 2008/0004578 A1    Jan. 3, 2008

(51) Int. Cl.
| | |
|---|---|
| *A61F 2/04* | (2013.01) |
| *A61L 31/14* | (2006.01) |
| *A61L 31/16* | (2006.01) |
| *A61M 27/00* | (2006.01) |
| *A61L 15/56* | (2006.01) |
| *A61F 13/42* | (2006.01) |

(Continued)

(52) U.S. Cl.
CPC ............ *A61L 31/148* (2013.01); *A61F 2/04* (2013.01); *A61L 31/16* (2013.01); *A61M 27/008* (2013.01); *A61F 13/34* (2013.01); *A61F 13/42* (2013.01); *A61F 2002/048* (2013.01); *A61F 2002/9528* (2013.01); *A61F 2013/422* (2013.01); *A61F 2250/0029* (2013.01); *A61F 2250/0031* (2013.01); *A61F 2250/0035* (2013.01); *A61F 2250/0079* (2013.01); *A61L 15/56* (2013.01); *A61L 2300/40* (2013.01)

(58) Field of Classification Search
CPC ............ A61F 2/04; A61F 2002/048; A61F 2002/9528; A61F 2250/0079; A61F 13/34; A61F 13/42; A61F 2013/422; A61M 27/008; A61L 15/56; A61L 31/148; A61L 31/16

USPC ........................ 623/1.42, 1.44, 1.46, 23.66, 623/23.64–23.7; 604/8–9; 62/1.42, 1.44, 62/1.46, 23.64, 23.7
See application file for complete search history.

(56) References Cited

U.S. PATENT DOCUMENTS

| | | |
|---|---|---|
| 3,780,740 A | 12/1973 | Rhea |
| 4,197,289 A | 4/1980 | Sturzenegger et al. |
| 4,526,804 A | 7/1985 | Escallon |

(Continued)

FOREIGN PATENT DOCUMENTS

| | | |
|---|---|---|
| DE | 10 2005 018356 A1 | 10/2006 |
| EP | 0 251 471 A1 | 1/1988 |

(Continued)

OTHER PUBLICATIONS

Globalrph. "Urine discoloration/Urinalysis". Medications which may cause discoloration of uring (Table). Downloaded from <www.globalrph.com/urine.htm> on Mar. 5, 2014.*

(Continued)

*Primary Examiner* — Andrew Iwamaye
(74) *Attorney, Agent, or Firm* — Kacvinsky Daisak Bluni PLLC

(57) ABSTRACT

A medical device includes an elongate body configured to be disposed within a urinary tract of a patient such that a first end portion of the elongate body is disposed at a first location of the urinary tract and a second end portion of the elongate body is disposed at a second, different location of the urinary tract. The elongate body defines a lumen that is configured to convey urine from the first location of the urinary tract to the second location of the urinary tract. An agent is formulated to visually alter urine of the patient, the agent is coupled to the elongate body and releasable into the patient's urine.

5 Claims, 9 Drawing Sheets

(51) Int. Cl.
*A61F 2/95* (2013.01)
*A61F 13/34* (2006.01)

(56) References Cited

U.S. PATENT DOCUMENTS

| | | | |
|---|---|---|---|
| 4,610,657 A * | 9/1986 | Densow | 604/8 |
| 4,692,152 A | 9/1987 | Emde | |
| 4,698,056 A | 10/1987 | Ciannella | |
| 4,790,310 A | 12/1988 | Ginsburg et al. | |
| 4,827,940 A | 5/1989 | Mayer et al. | |
| 4,830,279 A | 5/1989 | Crum et al. | |
| 4,876,126 A | 10/1989 | Takemura et al. | |
| 4,936,835 A | 6/1990 | Haaga | |
| 5,059,211 A | 10/1991 | Stack et al. | |
| 5,061,281 A | 10/1991 | Mares et al. | |
| 5,085,629 A | 2/1992 | Goldberg et al. | |
| 5,091,205 A | 2/1992 | Fan | |
| 5,368,588 A * | 11/1994 | Bettinger | 604/891.1 |
| 5,464,450 A | 11/1995 | Buscemi et al. | |
| 5,500,013 A | 3/1996 | Buscemi et al. | |
| 5,527,337 A | 6/1996 | Stack et al. | |
| 5,599,291 A * | 2/1997 | Balbierz et al. | 604/8 |
| 5,670,558 A | 9/1997 | Onishi et al. | |
| 5,695,826 A | 12/1997 | Escallon | |
| 5,714,007 A | 2/1998 | Pletcher et al. | |
| 5,769,276 A | 6/1998 | Alexander | |
| 5,814,006 A * | 9/1998 | Planz | 604/8 |
| 5,964,744 A * | 10/1999 | Balbierz et al. | 604/530 |
| 5,980,551 A | 11/1999 | Summers et al. | |
| 5,984,965 A * | 11/1999 | Knapp et al. | 623/23.7 |
| 6,120,491 A | 9/2000 | Kohn et al. | |
| 6,306,422 B1 | 10/2001 | Batich et al. | |
| 6,322,847 B1 | 11/2001 | Zhong et al. | |
| 6,355,058 B1 | 3/2002 | Pacetti et al. | |
| 6,368,658 B1 | 4/2002 | Schwarz et al. | |
| 6,372,246 B1 | 4/2002 | Wei et al. | |
| 6,379,382 B1 * | 4/2002 | Yang | 623/1.42 |
| 6,387,124 B1 | 5/2002 | Buscemi et al. | |
| 6,395,023 B1 | 5/2002 | Summers | |
| 6,494,916 B1 | 12/2002 | Babalola et al. | |
| 6,506,958 B2 * | 1/2003 | Williams | 604/361 |
| 6,537,256 B2 * | 3/2003 | Santini et al. | 604/191 |
| 6,656,146 B1 * | 12/2003 | Clayman et al. | 604/8 |
| 6,656,162 B2 * | 12/2003 | Santini et al. | 604/191 |
| 6,663,662 B2 | 12/2003 | Pacetti et al. | |
| 6,673,053 B2 | 1/2004 | Wang et al. | |
| 6,770,066 B1 | 8/2004 | Weaver et al. | |
| 2001/0001823 A1 | 5/2001 | Ryan | |
| 2002/0004060 A1 | 1/2002 | Heublein et al. | |
| 2002/0055757 A1 * | 5/2002 | Torre et al. | 606/192 |
| 2002/0138154 A1 * | 9/2002 | Li et al. | 623/66.1 |
| 2003/0083646 A1 * | 5/2003 | Sirhan et al. | 604/891.1 |
| 2003/0109930 A1 * | 6/2003 | Bluni et al. | 623/23.7 |
| 2003/0153901 A1 * | 8/2003 | Herweck et al. | 604/891.1 |
| 2003/0208256 A1 * | 11/2003 | DiMatteo et al. | 623/1.11 |
| 2003/0224033 A1 | 12/2003 | Li et al. | |
| 2004/0034409 A1 | 2/2004 | Heublein et al. | |
| 2004/0064116 A1 * | 4/2004 | Arora et al. | 604/361 |
| 2004/0098108 A1 | 5/2004 | Harder et al. | |
| 2004/0148007 A1 | 7/2004 | Jackson et al. | |
| 2004/0193092 A1 * | 9/2004 | Deal | 604/8 |
| 2004/0215169 A1 * | 10/2004 | Li | 604/537 |
| 2004/0234748 A1 | 11/2004 | Stenzel | |
| 2004/0249441 A1 * | 12/2004 | Miller et al. | 623/1.15 |
| 2005/0065596 A1 * | 3/2005 | Tseng et al. | 623/1.42 |
| 2006/0025726 A1 | 2/2006 | Fischer, Jr. et al. | |
| 2008/0183299 A1 * | 7/2008 | Monga et al. | 623/23.66 |

FOREIGN PATENT DOCUMENTS

| | | |
|---|---|---|
| EP | 1 543 798 A2 | 6/2005 |
| FR | 2 654 345 A | 5/1991 |
| WO | WO 99/24107 A1 | 5/1999 |
| WO | WO 01/23015 A1 | 4/2001 |
| WO | WO 01/49249 A2 | 7/2001 |
| WO | WO 03/068285 A2 | 8/2003 |
| WO | WO 2005/014069 A1 | 2/2005 |

OTHER PUBLICATIONS

Harvard Health Publications. "Red, brown, green: Urine colors what they might mean". Downloaded from <http://www.health.harvard.edu/newsletters/Harvard_Womens_Health_Watch/2010/June/urine-color-and-odor-changes> on Mar. 5, 2014.*
Guidant Acquires Majority Stake in Bioabsorbable Stent Company, Synecor, LLC, Apr. 1, 2003, [online], http://www.synecor.com/news/biostent.html, 2 pages.
Natsios, J., The Physical Parameters that Govern Stent-Based Local Drug Delivery, Biotechnology and Engineering Production Group, Apr. 29, 2003, 3 pages.
REVA Medical, Inc. and the New Jersey Center for Biomaterials collaborate to develop the first fully resorbable polymer drug delivery stent that is visible by X-ray, REVA Medical, Inc., Sep. 15, 2003, [online], http://www.md3inc.com/company_news_xray.html, 2 pages.
Conor Medsystems and Biotronik Agree to Develop Bioabsorbable Drug Eluting Stent, Conor Medsystems, Inc., May 27, 2004, [online], http://www.zurichmednet.org/development/BioabsorableDrug.htm, 2 pages.
Bertrand, O. et al., Biomechanics of Coronary Stents, Jul. 15, 2004, 2 pages.
Hydromer Stent Coatings, Hydromer, Jul. 15, 2004, [online], http://www.hydromer.com/stent_coatings.htm, 2 pages.
Rhodes, W. E., III, Advanced Delivery Devices, Drug-Eluting Stents for Localized Delivery—Getting to the Heart of the Problem, Drug Delivery Technology, Jul. 15, 2004, [online], http://www.drugdeliverytech.com/cgi-bin/articles.cgi?idArticle=38, 3 pages.
REVA Medical Design for Life, Jul. 19, 2004, 7 pages.
Resorbable Biodegradable Stent, BioScorpio, Jul. 20, 2004, 2 pages.
Triumphant Technology, TyRx Pharma Inc., Aug. 27, 2004, 4 pages.
International Search Report and Written Opinion for International Application No. PCT/US2007/064745, mailed on Jun. 26, 2008, 15 pages.

* cited by examiner

STENT HAVING TIME-RELEASE INDICATOR

BACKGROUND

The disclosed invention relates generally to a medical device and more particularly to a ureteral stent having an agent configured to visually alter the urine of a patient.

Known ureteral stents are typically placed within a urinary tract of a patient such that one end portion of the ureteral stent is located in either a kidney or a ureter of the patient and another end portion of the ureteral stent is located in a bladder of the patient. Some known ureteral stents include retention members configured to help retain the ureteral stent in position within the patient. Known ureteral stents are typically positioned within the urinary tract of the patient by placing a guidewire within the patient, sliding the ureteral stent on the guidewire, and then forcing the ureteral stent along the guidewire into a desired position within the patient using a push cannula. After an appropriate period of time, the ureteral stent is removed from the patient, such as by pulling the ureteral stent from the urinary tract of the patient.

A problem associated with the use of such known ureteral stents is that a patient may forget the stent is disposed within the patient's body, and/or the patient may delay returning to a physician to have a stent removed after the appropriate period of time. When this situation occurs, the stent may become encrusted or otherwise blocked, causing a loss of fluid passage through the stent and possible loss of kidney function. Thus, it would be desirable for a stent to provide an indicator to alert the patient that it is time for the stent to be removed.

A recent development in stents is to form the stent from a biodegradable material, such that the stent dissolves or degrades in situ in the patient's urinary tract. This avoids the need to remove the stent. It would be desirable to have a way to monitor the status of the stent, such as whether the stent is still present in the patient's urinary tract.

SUMMARY OF THE INVENTION

A ureteral stent includes an elongate body configured to be disposed within a urinary tract of a patient such that a first end portion of the elongate body is disposed at a first location of the urinary tract and a second end portion of the elongate body is disposed at a second, different location of the urinary tract. The elongate body defines a lumen that is configured to convey urine from the first location of the urinary tract to the second location of the urinary tract. An agent is formulated to visually alter urine of the patient, the agent is coupled to the elongate body and releasable into the patient's urine.

BRIEF DESCRIPTION OF THE DRAWINGS

The present invention is described with reference to the accompanying drawings.

DETAILED DESCRIPTION

Figure 1:
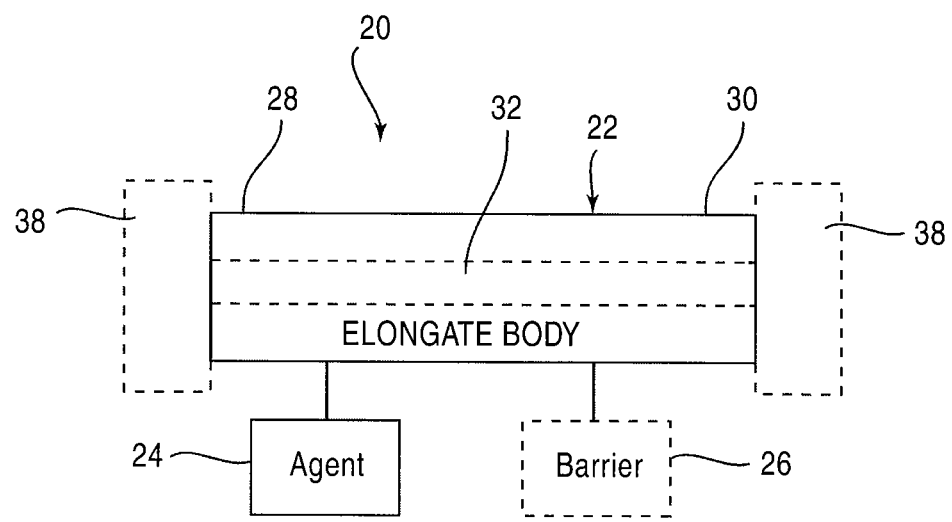
FIG. 1 is a schematic illustration of a stent according to an embodiment of the invention.

FIG. 1 is a schematic illustration of a stent according to an embodiment of the invention. A stent 20 is configured to be placed or otherwise implanted (transuretherally or percutaneously) into a urinary tract of a mammalian body.

The stent 20 can include any of the conventional structures of a ureteral stent. In the embodiment illustrated schematically in FIG. 1, stent 20 includes an elongate body 22 defining a lumen 32 extending from a proximal end portion 28 to a distal end portion 30, through which urine may be conveyed. The elongate body 22 and lumen 32 can be configured in any of the conventional configurations for a ureteral stent. Similarly, each of the proximal end portion 28 and distal end portion 30 can be configured, or can include a retention member 38, to provide retention of the stent 20 within the urinary tract. The stent 20 can be disposed within the urinary tract of the patient such that the proximal end portion 28 is disposed within either a ureter or a bladder of a patient and the distal end portion 30 is disposed within either the ureter or a kidney of the patient. The elongate body 22 can include one or more openings (not shown in FIG. 1) in communication with the lumen 32 defined by the elongate body 22. For example, the elongate body 22 can include openings along a side wall of the elongate body 22 and/or on an end of the elongate body 22. The elongate body 22 can also include more than one lumen.

The elongate body 22 can be constructed with a variety of different materials such as biocompatible plastics and/or metals. The elongate body 22 may consist of one material or may be formed, for example by extrusion, of two or more materials along its length. For example, in one embodiment, the distal end portion 30 of the elongate body 22 is formed from a first material having a first durometer and the proximal end portion 28 is formed from a second material. Accordingly, the proximal end portion 28 may be made of a softer or more flexible material than that of the distal end portion 30, and vice versa.

The elongate body 22 may be formed from any material or materials known in the art to be used in constructing ureteral stents. One subset of biocompatible materials best suited for the elongate body 22 exhibit at least some of the following characteristics: high tensile strength, high retention coil strength, excellent biocompatibility and biodurability, excellent radiopacity or fluoroscopic visibility, availability in varying durometers, and a low resistance to passage. For example, in one embodiment, the elongate body 22 is formed from a polymeric material, such as polyactic acid, polyglycolic acid, collagen, polycaprolactone, hylauric acid, adhesive protein, co-polymers of these materials, as well as composites and combinations thereof.

The elongate body 22 can also be formed of a variety of different bioabsorbable or biodegradable materials. For example, the stent 20 can be formed of a bioabsorbable polymer. Known bioabsorbable polymer stents include the stents disclosed in U.S. Pat. Nos. 5,464,450; 6,387,124; and 5,500,013 (the disclosures of which are incorporated herein by reference in their entirety). Suitable polymers include, for example, poly-L-lactides, Ethyl vinyl acetate, and polyamides.

Stent 20 also includes a visual indicator agent 24. The agent 24 is formulated to alter the appearance of the patient's urine when it is released into the urinary tract of the patient. For example, the agent 24 can be formulated to change the color of the urine. Thus, when the agent 24 is released into the urinary tract of the patient, the patient will notice the changed appearance of the urine discharged by the patient and be alerted or reminded about the existence of the stent 20 within the urinary tract of the patient. The agent 24 can include, but is not limited to, FD&C Red No. 40, Allura Red AC, FD&C Blue No. 2, and Indigotine powder.

The agent 24 can be coupled to, included in, or incorporated into, stent 20 in a variety of ways. The agent 24 may be separate from the material of stent 20, in any suitable form (solid, liquid, or gas) in a reservoir, coating, or other discrete body, or may be incorporated directly into some or all of the materials of, and/or portions of, stent 20.

Stent 20 may be configured, and/or agent 24 may be formulated, such that agent 24 is released into the urinary tract immediately upon placement of the stent 20 into the patient's urinary tract, or such that it is not released into the urinary tract until after the passage of some time after placement of the stent 20. Similarly, stent 20 may be configured, and/or agent 24 may be formulated, such that agent 24 is released into the urinary tract for a longer or shorter, finite period of time, or for the duration of the stent's presence in the patient's urinary tract. Thus, for example, in the case where stent 20 is formed of biodegradable materials, agent 24 may be incorporated into stent 20 such that it is released into the patient's urinary tract continually until the stent has completely biodegraded or dissolved, thus providing a continuing visual indicator to the patient that the stent is in the patient's urinary tract. If the patient's urine does not return back to a normal appearance after a specified amount of time, this can be an indication to the patient that there is a problem (because the stent has not completely biodegraded) and that they should notify their physician.

If the release of agent 24 is to be delayed until some time after placement of stent 20 in the patient's urinary tract, stent 20 can include an inhibitor or barrier 26 disposed to separate agent 24 from the urinary tract (such as the urine within the tract) until the agent 24 is to be released. Barrier 26 may be a dissolvable or degradable coating disposed over a layer of agent 24 in solid form or over the surface of the portion of stent 20 in which agent 24 is incorporated, or a membrane covering an opening into a reservoir containing agent 24.

Barrier 26 can be formed of a variety of different biocompatible and/or bioabsorbable or biodegradable materials. For example, the barrier 26 can be formed of any suitable polymer material, and/or suitable bioabsorbable polymers as discussed above for the elongate body 22. The barrier 26 can also be formed, for example, with a collagen based gelatin, or a compacted salt polymer mix.

The rate of release of agent 24 from stent 20 can be selected, and varied over time if desired, by selecting appropriate values for variables including the formulation and form of agent 24, the thickness, absorption rate, and portion of agent 24 protected by barrier 26, and/or the absorption rate of the material(s) and portion(s) of stent 20 into which agent 24 is incorporated. The rate of release of agent 24 can also be affected by the nature and condition of the tissue and/or bodily fluid with which the barrier 26 or elongate body 22 is in contact. For example, the physiochemical properties of the body lumen, such as the pH of urine of the patient, can affect the rate of release of agent 24 and/or the rate of dissolution or degradation of barrier 26. The geometry and/or composition of barrier 26 and/or agent 24 may be selected to reflect such properties of the body lumen. For example, in one of several alternative components, each including agent 24 in various formulations (e.g., solid or liquid form), and each with an associated barrier 26, may be selected for attachment to the stent 20 immediately prior to insertion into the patient's urinary tract, based on a measurement of the relevant property(ies) of the urinary tract.

Having described above various general principles, several exemplary embodiments of these concepts are now described. These embodiments are only exemplary, and many other configurations and formulations of elongate body 22, agent 24, and barrier 26, are contemplated by the principles of the invention, and will be apparent to the artisan in view of the general principles described above and the exemplary embodiments.

Figure 4:
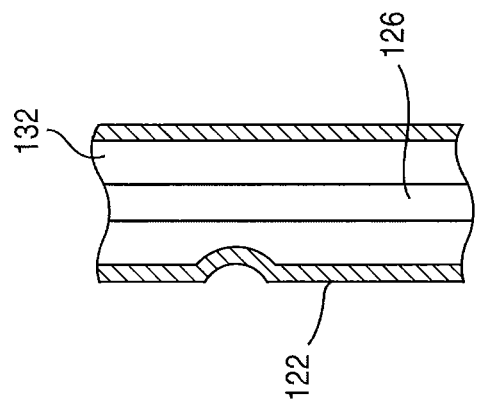
FIG. 4 is a cross-sectional view taken along line 4-4 in FIG. 2.
Figure 3:
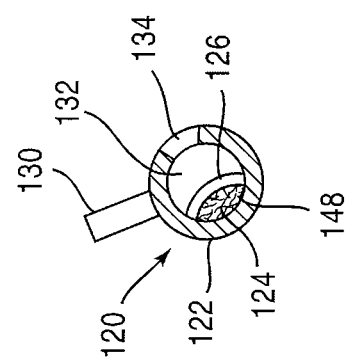
FIG. 3 is a cross-sectional view taken along line 3-3 in FIG. 2.
Figure 2:
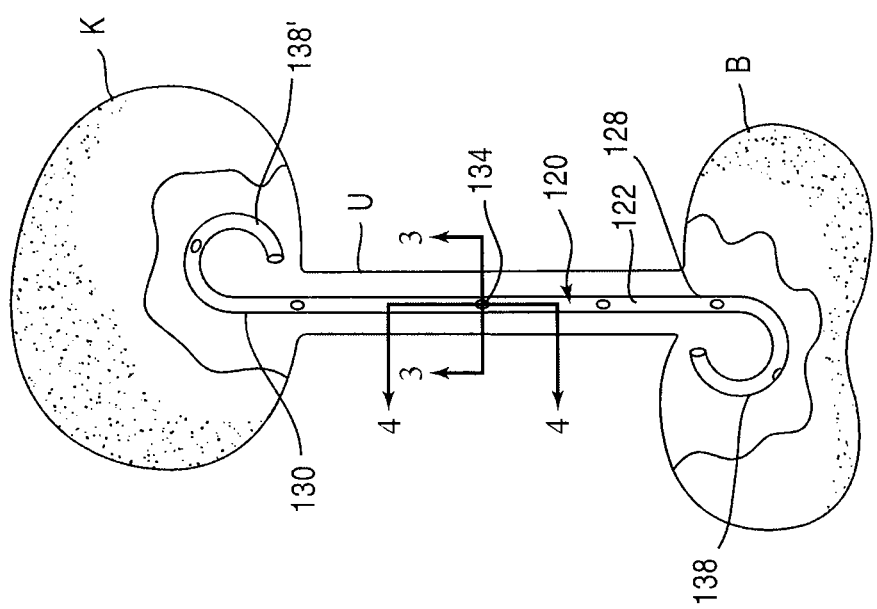
FIG. 2 is a side perspective view of a stent according to an embodiment of the invention shown disposed within a urinary tract of a patient.

FIGS. 2-4 illustrate a stent 120 according to one embodiment of the invention. The stent 120 includes an elongate body 122 having a proximal end portion 128, a distal end portion 130 and defining a lumen 132 (see FIG. 3). The proximal end portion 128 includes a retention member 138 and is disposable within a bladder B of a patient, and the distal end portion 130 includes a retention member 138' and is disposable within a kidney K of the patient. When positioned within the body of the patient, the stent 120 extends from the kidney K through the ureter U and into the bladder B. The retention members 138 and 138' help retain the stent 120 in this position within the urinary tract of the patient.

The elongate body 122 also defines a plurality of openings 134 in communication with the lumen 132. The openings 134 and the lumen 132 permit the flow of fluid, e.g. urine, through the stent 120.

The stent 120 also includes a reservoir 148 containing an agent 124, disposed within the elongate body 122 and separated from the lumen 132 by a barrier or coating 126, as shown in FIGS. 3 and 4. The barrier 126 is formed from a suitable material that is soluble in urine, such that after an appropriate time after the stent is disposed within the urinary tract of the patient, the barrier 126 dissolves sufficiently to release the agent 124 from reservoir 148 into the lumen 132 and thence into the urinary tract of the patient. The agent 124 is formulated to visually alter the appearance of the urine, such as by changing the color of the urine. The agent 124 is thus an indicator to the patient that the stent 120 is still disposed within the patient's body. The agent 124 may be in a solid form, applied to, or disposed on, an inner surface of elongate body 122, with barrier 126 applied over the agent 124 as a coating to prevent urine in lumen 132 from contacting it. When the barrier 126 is dissolved, exposing the agent 124 to the urine, the urine begins to dissolve the agent 124, so that it forms a solution with the urine. Depending on the rate at which the agent 124 dissolves in the urine, the urine may be visually altered (e.g. colored) by the agent 124 to a greater or lesser degree, and for a correspondingly shorter or longer period of time. Alternatively, the agent 124 may be in a fluid form, and contained within reservoir 148 formed and bounded by the inner wall of the elongate member 122 and the barrier 126. When barrier 126 is sufficiently dissolved by the urine, it ruptures, and releases the agent into lumen 132 and thence into the urinary tract, mixed with the urine.

Figure 6:
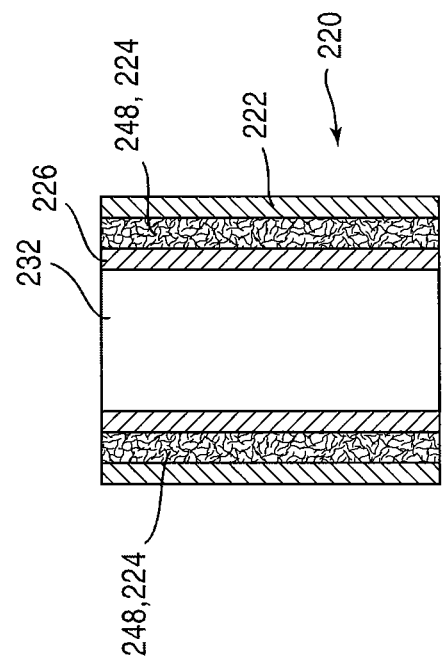
FIG. 6 is a cross-sectional view taken along the line 6-6 in FIG. 5.
Figure 5:
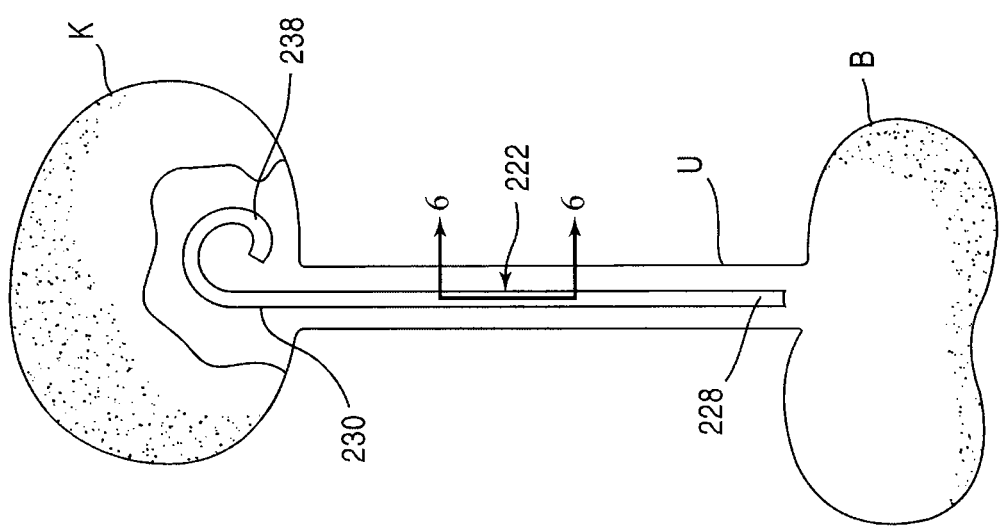
FIG. 5 is a side perspective view of a stent according to an embodiment of the invention shown disposed within a urinary tract of a patient.

FIGS. 5 and 6 illustrate a stent according to another embodiment of the invention. A stent 220 is shown disposed within a urinary tract of a patient. The stent 220 includes an elongate body 222 having a proximal end portion 228 configured to be disposed within a ureter U of a patient, and a distal end portion 230 configured to be disposed in a kidney K of the patient. In this embodiment, only the distal end portion 230 includes a retention member 238 to retain the stent within the kidney K. The elongate body 222 also defines a lumen 232 shown in FIG. 6. In this embodiment, a barrier 226 is disposed concentrically within an inner wall of the elongate body 222 to form an annular reservoir 248 containing an agent 224. As with the previous embodiment, agent 224 can be a solid or a fluid.

FIGS. 7-9B illustrate a stent according to another embodiment of the invention. A stent 320 includes an elongate body 322 having a proximal end portion 328 configured to be disposed within a bladder of a patient and a distal end portion 330 configured to be disposed within a kidney of a patient. In this embodiment, both the proximal end portion 328 and the distal end portion 330 include retention members 338 and 338' to help retain the stent 20 in position within a urinary tract. The elongate body 322 defines a first lumen 332, a second lumen 336 and a plurality of openings 334 in communication with the second lumen 336.

Figures 7, 8:
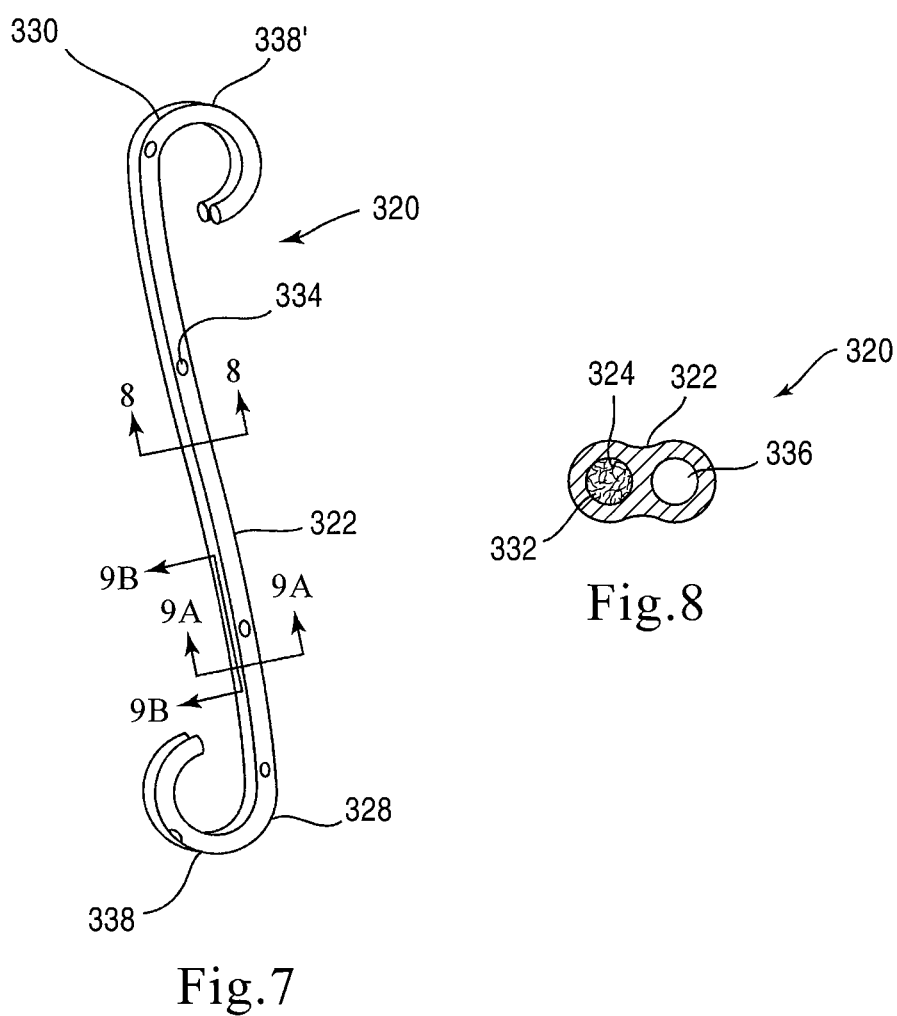
FIG. 7 is a side perspective view of a stent according to another embodiment of the invention.
FIG. 8 is a cross-sectional view taken along line 8-8 in FIG. 7.
Figure 9A:
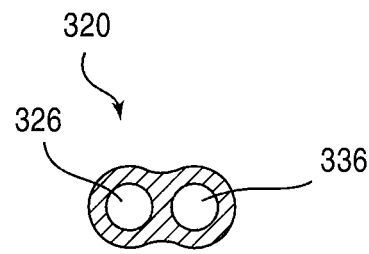
FIG. 9A is a cross-sectional view taken along line 9A-9A in FIG. 7.
Figure 9B:
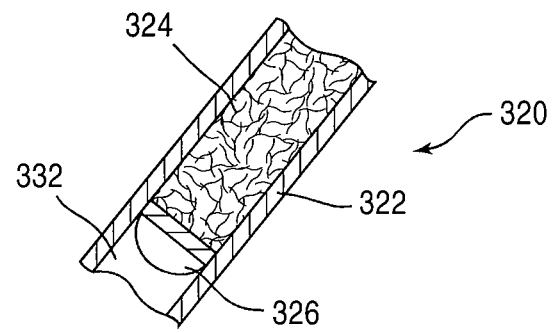
FIG. 9B is a sectional view taken along line 9B-9B in FIG. 7.

In this embodiment, first lumen 332 is a reservoir for an agent 324 (as shown in FIGS. 8 and 9B), and a barrier 326 is disposed across the first lumen 332 to form a seal over the agent 324 (as shown in FIGS. 9A and 9B). Barrier 326 thus separates the agent 324 in lumen 332 from the urinary tract of the patient. As the barrier 326 is dissolved by urine, at least a portion of the agent 324 is released into the urinary tract of the patient. The barrier 326 can be included as a single seal configuration, closing off communication between the first lumen 332 and the urinary tract at a single location, or can alternatively be located in two locations, closing off two open portions of the lumen 332. For example, a coating 326 can be disposed at two locations within the lumen 332. In some embodiments, the coating 326 can be disposed at a distal end and/or a proximal end of the elongate body 322, rather than at a location a distance from the distal end and/or proximal end of the elongate body 322.

Figures 10, 11:
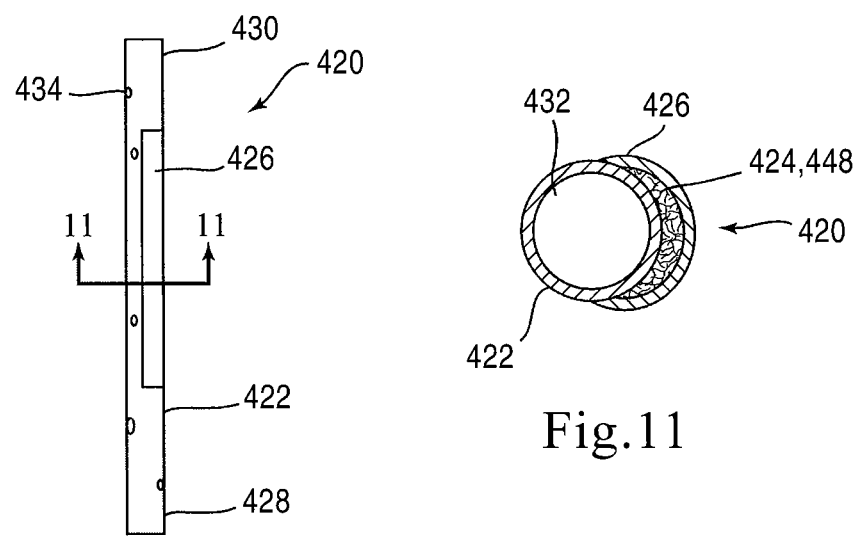
FIG. 10 is a side perspective view of a stent according to another embodiment of the invention.
FIG. 11 is a sectional view taken along line 11-11 in FIG. 10.

FIGS. 10 and 11 illustrate a stent according to another embodiment of the invention. A stent 420 includes an elongate body 422 having a proximal end portion 428, a distal end portion 430 and defining a lumen 432. The proximal end portion 428 and the distal end portion 430 of the stent 420 do not include a retention member. In this embodiment, the distal end portion 430 can be positioned within a ureter of a patient or within a kidney of the patient, and the proximal end portion 428 can be positioned within the ureter of the patient or within a bladder of the patient. In this embodiment, a reservoir 448 for an agent 424 is formed on the outside of the elongate body 422, between an outer wall of the elongate body 422 and a barrier 426. The reservoir 448 for the agent 424 need not be formed on, or as part of, the elongate body 422.

Figure 13A:
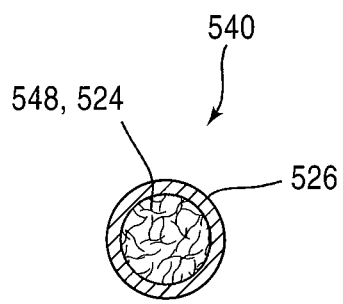
FIG. 13A is a cross-sectional view taken along line 13-13 in FIG. 12.
Figure 13B:
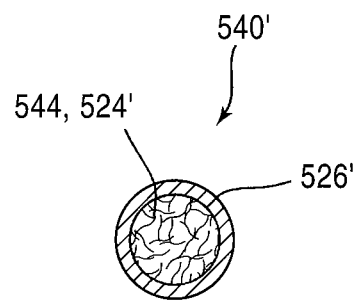
FIGS. 13B and 13C are cross-sectional views of portions of stents according to other embodiments of the invention.
Figure 13C:
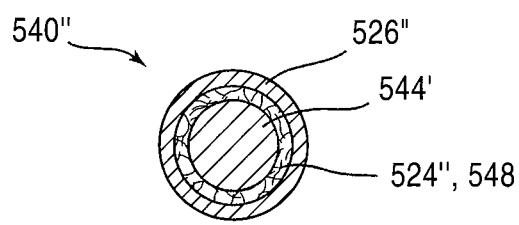
Figures 14, 15:
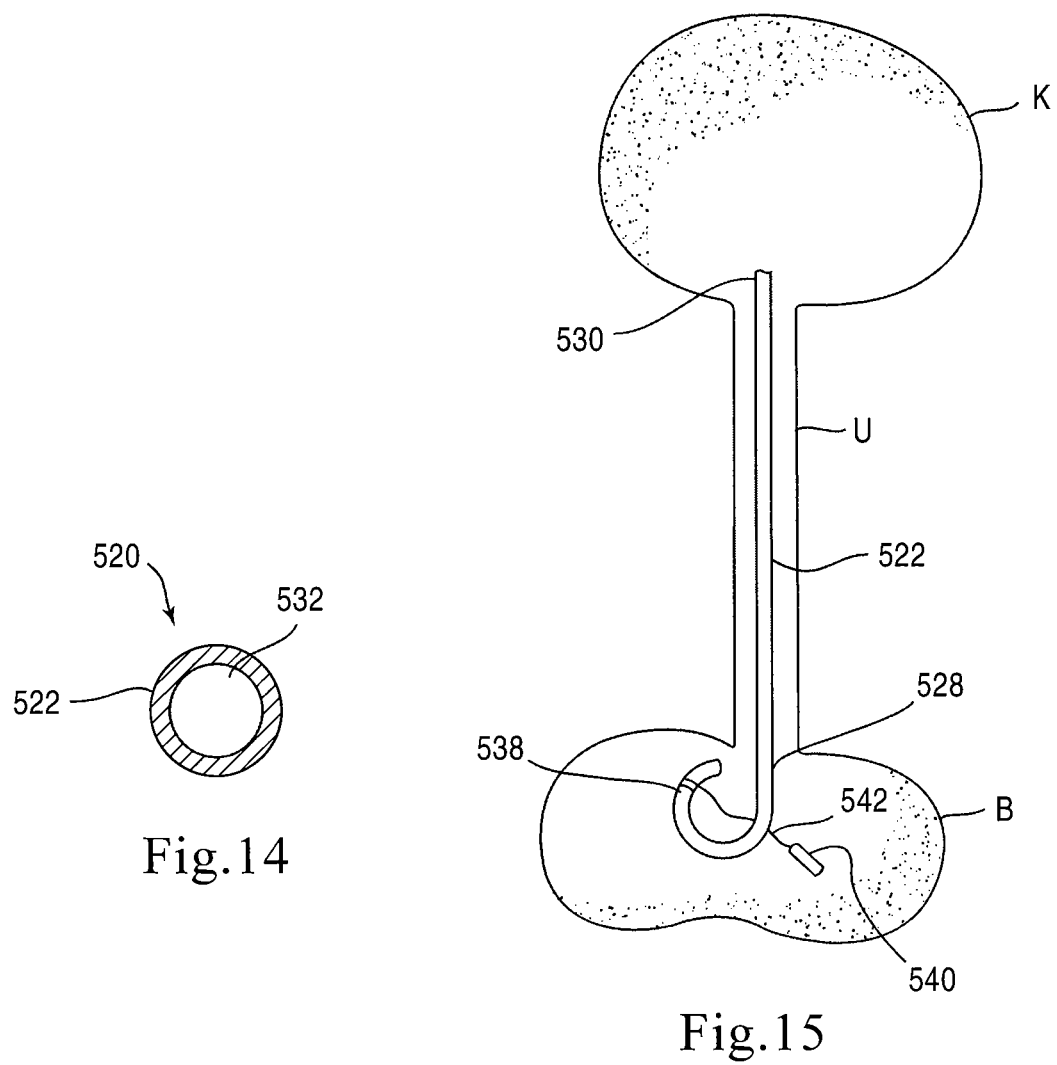
FIG. 14 is a cross-sectional view taken along line 14-14 in FIG. 12.
FIG. 15 is a side perspective view of the stent shown in FIG. 12 shown disposed within a urinary tract.

FIGS. 12-15 illustrate a ureteral stent according to another embodiment of the invention. A stent 520 includes an elongate body 522 having a proximal end portion 528 configured to be disposed within a bladder B of a patient, a distal end portion 530 configured to be disposed within a kidney K of the patient, and defines a lumen 532 (as shown in FIG. 14). In this embodiment, only the proximal end portion includes a retention element 538.

Figure 12:
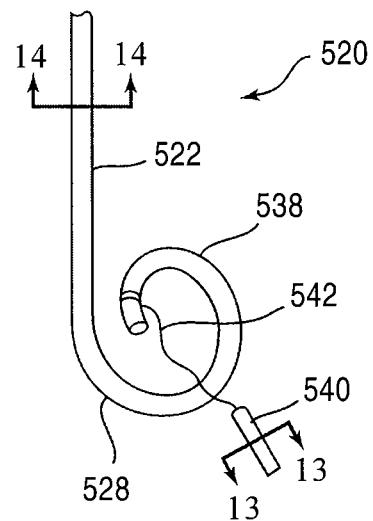
FIG. 12 is side perspective view of a portion of a stent according to an embodiment of the invention.

As shown in FIG. 12, a release element 540 is coupled to the proximal end portion 528 of the elongate body 522 with a tether 542. As shown in FIG. 13A, the release element 540 includes a coating or barrier 526 defining a cavity or reservoir 548 in which an agent 524 can be disposed. The release element 540 performs a similar function to the reservoir and barrier combinations described in the previous embodiments, but is separate from, though tethered to, the elongate body 522. The agent 524 is released from the release element 540 and into a urinary tract of a patient in a similar manner as described above, and as described in more detail below.

The tether serves to couple the release element to the elongate member 522 so that it is maintained within the urinary tract. The tether can be formed with a variety of different materials such as, for example, braided nylon or polyester fiber. Alternatively, the release element 540 can be coupled to the distal end portion 530, or at any other suitable location on the elongate body 522. Although a tether 542 is illustrated, other suitable coupling methods can be used.

In some embodiments, a release element 540' can include a barrier or coating 526' and a base 544, as shown in FIG. 13B. The base 544 can include, for example, an agent 524' incorporated within the material used to construct the base 544. For example, the base 544 can be constructed with a permeable material, such as an absorbable foam or fabric material that can carry the agent 524' therein. Alternatively, a release element 540" can include a base 544' that is non-permeable, and a coating 526" as shown in FIG. 13C. In this embodiment, the base 544' and the barrier 526" define a reservoir 548 in which an agent 524" can be disposed.

The barrier 526 (526', 526") disposed on a release element 540 (540', 540") can have various thicknesses, which will alter the rate of absorption or degradation of the barrier 526 (526', 526"). For example, a thicker barrier 526 (526', 526") can provide a slower rate of absorption or degradation, and/or a longer delay before the onset of absorption or degradation, than a barrier 526 (526', 526") having a thinner coating. Thus, the release element 540 (540', 540") can be configured with a particular rate of absorption or degradation of the barrier 526 (526', 526") and, therefore, different time periods for release of the agent 524 (524', 524") into the urinary tract of the patient. As stated previously, the rate of absorption or degradation of the barrier can be affected by, for example, the physiology of the patient, and the thickness and amount of the barrier. Depending on the particular patient physiology, such as the pH of urine of the patient, a particular configuration of release elements 540 (540', 540") may be needed. For example, a first patient may have a urine pH of 6.5 and the physician desire that the stent remain in the patient's body for a time period of, for example, one week. The physician can select a release element 540 (540', 540") that will achieve the desired time release of the agent 524 (524', 524") for that particular patient's pH level and thus remind the patient of the existence of the stent at the desired time. Therefore it may be desirable to package a single stent with multiple release elements, so that the physician can select, and attach to the stent, a release element that provides the desired delay before release of the agent.

In an alternative embodiment, a stent can include multiple reservoirs defined by one or more barriers/coatings, and the reservoirs can contain multiple different agents. For example, such a stent can be configured to change the appearance of the urine to a first state (e.g., appearance, such as an orange color) after a first time period, to a second state (such as a purple color) after a second time period, and to a third state (such as a blue color) after a third time period. Such a stent can convey to the patient different levels of urgency to remove the stent based on the changed appearance of the urine.

In another embodiment, an absorbable or degradable stent can include multiple layers, with each layer incorporating a different agent. Similar to the previous embodiment, as the various layers are absorbed or degraded, the different agents are released into the urinary tract, conveying information to the patient as to the condition or state of absorption of the stent.

Figure 16:
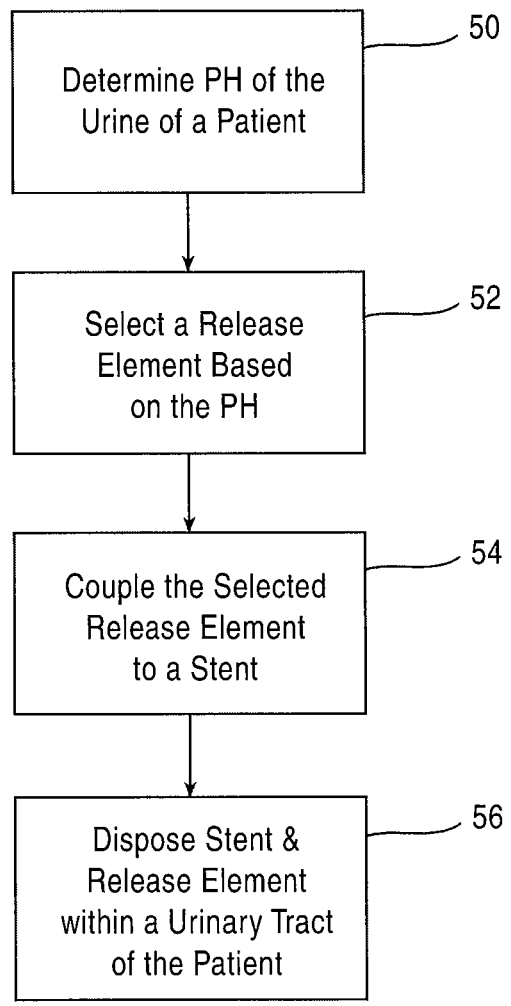
FIG. 16 is a flowchart illustrating a method according to an embodiment of the invention.

A method of configuring a ureteral stent according to an embodiment of the invention is illustrated in the flowchart of FIG. 16. The pH of urine of a patient can be tested and determined at step 50. At step 52, a release element can be selected from a plurality of release elements having different configurations. The plurality of release elements can each have a different thickness of an absorbable or degradable barrier or coating and/or a different rate of absorption/degradation of the barrier/coating. The selection of a particular release element can be based on the pH of the urine of the patient. At step 54, the release element can then be coupled to a stent that is configured to be disposed within a urinary tract of a patient. The release element can be coupled to the stent via a tether or other suitable coupling. The stent (with the release element) can then be disposed within a urinary tract of a patient at step 56. After a time period determined by the configuration of the stent and the release element, the coating disposed on the release element will at least partially dissolve or be biodegraded (or bioabsorbed) within the body of the patient, and an agent will be released within the urinary tract of the patient. The agent can alter the appearance of the urine of the patient, by, for example, altering the color of the urine. This change of color of the urine will alert or remind the patient that the stent is disposed within the patient's body and may need to be removed.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention. For example, the various features of ureteral stent 20 (120, 220, 320, 420, 520) may include other configurations, shapes and materials not specifically illustrated, while still remaining within the scope of the invention.

What is claimed is:

1. A medical device, comprising:
a ureteral stent including an elongate body, the elongate body being configured to be disposed within a urinary tract of a patient such that a first curved retention member of the elongate body is disposed in a kidney of the patient to help retain the medical device in place within the urinary tract and a second curved retention member of the elongate body is disposed in a bladder of the patient to help retain the medical device in place within the urinary tract, the elongate body defining a lumen, the lumen being configured to convey urine from the kidney to the bladder;
a release element including a base member and a barrier member, the barrier member disposed around the base member, the barrier member formed with a biodegradable material, the barrier member and the base member collectively defining a reservoir therebetween;
a liquid agent disposed within the reservoir, the agent formulated to visually alter urine of the patient upon degradation of the barrier member by contact with the patient's urinary tract or urine therein; and
a tether having a first end portion coupled to the second curved retention member of the elongate body and a second end portion coupled to the release element, the tether being configured to allow the release element to move with respect to the elongate body.

2. The medical device of claim 1, wherein the liquid agent is formulated to visually alter a color of a patient's urine.

3. The medical device of claim 1, wherein the reservoir is annularly disposed between the base member and the barrier member.

4. The medical device of claim 1, wherein the release element is configured to be entirely disposed within a bladder of the patient when at least a portion of the elongate body is disposed in a ureter of the patient.

5. The medical device of claim 1, wherein the tether is configured to allow the release element to move with respect to the elongate body such that a longitudinal axis defined by the release element is non-parallel to a longitudinal axis defined by the elongate body.

* * * * *